(12) United States Patent
Rizun

(10) Patent No.: US 11,547,688 B2
(45) Date of Patent: Jan. 10, 2023

(54) AMINO ACID COMPOSITIONS AND METHODS OF MANUFACTURING THE COMPOSITIONS

(71) Applicant: Nodari Rizun, San Diego, CA (US)

(72) Inventor: Nodari Rizun, San Diego, CA (US)

(*) Notice: Subject to any disclaimer, the term of this patent is extended or adjusted under 35 U.S.C. 154(b) by 155 days.

(21) Appl. No.: 17/000,177

(22) Filed: Aug. 21, 2020

(65) Prior Publication Data

US 2021/0052534 A1 Feb. 25, 2021

Related U.S. Application Data

(60) Provisional application No. 62/890,531, filed on Aug. 22, 2019.

(51) Int. Cl.

| | | |
|---|---|---|
| *A61K 31/197* | (2006.01) | |
| *A61K 31/198* | (2006.01) | |
| *A61K 31/675* | (2006.01) | |
| *A61K 38/02* | (2006.01) | |
| *A61P 25/28* | (2006.01) | |
| *A61K 47/12* | (2006.01) | |
| *A61K 38/06* | (2006.01) | |
| *A61K 9/00* | (2006.01) | |
| *A61K 47/24* | (2006.01) | |

(52) U.S. Cl.
CPC .......... *A61K 31/198* (2013.01); *A61K 9/0053* (2013.01); *A61K 9/0095* (2013.01); *A61K 31/197* (2013.01); *A61K 31/675* (2013.01); *A61K 38/06* (2013.01); *A61K 47/12* (2013.01); *A61K 47/24* (2013.01); *A61P 25/28* (2018.01)

(58) Field of Classification Search
CPC ........ A23L 33/175; A23L 23/15; A23L 33/30; A23L 33/40; A61K 9/0053; A61K 9/0095; A61K 31/185; A61K 31/197; A61K 31/198; A61K 38/06; A61K 31/675; A61P 25/28; C07K 5/0815; C07K 5/0819
See application file for complete search history.

(56) References Cited

U.S. PATENT DOCUMENTS

| | | | | |
|---|---|---|---|---|
| 6,008,221 A * | 12/1999 | Smith | ...................... | A61P 25/28 514/250 |
| 7,504,376 B2 * | 3/2009 | Harris | ................... | A61K 31/385 514/400 |
| 8,324,278 B2 * | 12/2012 | Dioguardi | ............... | A61P 25/00 514/561 |
| 2002/0122835 A1 * | 9/2002 | Bucci | ..................... | A61K 31/315 424/734 |
| 2003/0211172 A1 * | 11/2003 | Jones | ..................... | A61K 33/04 514/276 |
| 2004/0248771 A1 * | 12/2004 | Raggi | ..................... | A61P 25/24 514/561 |
| 2006/0154871 A1 * | 7/2006 | Georgiades | ............. | A61P 31/12 514/4.8 |
| 2007/0286909 A1 | 12/2007 | Smith et al. | | |
| 2008/0193591 A1 * | 8/2008 | Wada | ....................... | A23L 27/45 426/649 |
| 2011/0064720 A1 * | 3/2011 | Amato | .................. | A61K 31/295 514/642 |
| 2011/0183040 A1 * | 7/2011 | Ermolin | .................. | A61P 17/00 426/657 |
| 2013/0142769 A1 * | 6/2013 | Smith | ..................... | A61P 25/00 424/94.1 |
| 2013/0171294 A1 * | 7/2013 | Martyn | ..................... | A23L 2/52 426/71 |
| 2014/0343112 A1 | 11/2014 | Ferrando et al. | | |
| 2015/0366935 A1 * | 12/2015 | Comiskey | ............ | A61K 9/2054 514/21.1 |
| 2017/0340694 A1 * | 11/2017 | Pitcher | ................... | A61K 33/24 |
| 2018/0258385 A1 * | 9/2018 | Rao | ........................ | C07K 14/34 |
| 2019/0144500 A1 * | 5/2019 | Expósito | .................. | C07K 7/06 424/637 |
| 2020/0138783 A1 * | 5/2020 | Rinaldi | ................ | A61K 31/714 |

FOREIGN PATENT DOCUMENTS

WO   WO-03035027 A1 *   5/2003   ............. A61K 33/10

OTHER PUBLICATIONS

Douglas Laboratories, "Free Form Amino Caps", retrieved from https://www.pureformulas.com/...24&CATARGETID=530005240008781124&cadevice=c&gclid=EAlaIQobChMlhPnns5-X4wlVghh9Ch2eBg_PEAQYASABEgJ70fD_BwE, on Jul. 25, 2019, in 6 pages.

Garcia et al., "Chirality Effects on Peptide Self-Assembly Unraveled from Molecules to Materials", (2018) Chem 4:1862-1876, https://doi.org/10.1016/j.chempr.2018.05.016, in 67 pages.

Ming, Ni, "Ultrashort peptides: minimum No. in amino acid residues, maximum No. in bioapplications", (2019) Bionatura 4(1):763-764, http://www.revistabionatura.com DOI, 10.21931/RB/2019.04.01.1, in 2 pages.

Onnit Labs, Inc., "Alpha Brain", retrieved from https://www.onnit.com/alphabrain/ on Jul. 25, 2019, in 24 pages.

Technical University of Munich (TUM), "Breakthrough for peptide medication: The 'Holy Grail' of peptide chemistry: New strategy makes peptide active agents available orally", (2018) ScienceDaily, in 4 pages.

* cited by examiner

*Primary Examiner* — Jeffrey E. Russel
(74) *Attorney, Agent, or Firm* — Procopio, Cory, Hargreaves & Savitch LLP

(57) ABSTRACT

Nootropic compositions and methods of providing or using the same are provided herewith. Some preferred compositions include a combination of free amino acids and one or more peptides. Compositions may optionally include one or more of an anti-adherent, a B vitamin, shilajit, a sugar, a fatty acid, ashwaganda, ginseng, or rodiola, among other things.

9 Claims, No Drawings

AMINO ACID COMPOSITIONS AND METHODS OF MANUFACTURING THE COMPOSITIONS

CROSS REFERENCE TO RELATED APPLICATIONS

This application claims priority to U.S. provisional patent application Ser. No. 62/890,531, filed on Aug. 22, 2019. This and all other extrinsic materials discussed herein are incorporated by reference in their entirety. Where a definition or use of a term in an incorporated reference is inconsistent or contrary to the definition of that term provided herein, the definition of that term provided herein applies and the definition of the term in the reference does not apply.

FIELD OF THE INVENTION

The field of the invention is amino acid compositions, such as nootropic amino acid compositions, compositions supporting a vegan lifestyle, and compositions for supporting brain health.

BACKGROUND

Some compositions comprising specific amino acids are known for attempting to treat one or more disorders associated with a deficiency of an amino acid. For example, US Patent Application Publication No. 2007/0286909 teaches a composition comprising a homogenous mixture of certain free amino acids in an attempt to treat insomnia, soft tissue injury, and emotional distress. Some compositions comprising specific amino acids are known for attempting to improve recovery of muscle strength and function. For example, US Patent Application Publication No. 2014/0343112 teaches a composition comprising specific concentrations of specific amino acids in an attempt to improve muscle strength and function.

Unfortunately, some known compositions can require that users take numerous doses of numerous formulations or pills for extended periods of time with little or no improvement in treating or preventing certain disorders.

The present disclosure is directed toward one or more improved features identified below, and to devices and systems that address the above-mentioned problems.

SUMMARY

The inventive subject matter provides oral amino acid and peptide formulations/compositions, and methods of using such formulations/compositions. In some contemplated aspects, the oral composition is effective in supporting brain health, preventing, treating, or relieving a sign or symptom associated with one or more conditions, including for example, attention deficit/hyperactivity disorder, memory dysfunctions, learning disabilities, delays in speech development, depression, or epilepsy, conditions of decreased physical and mental power, negative schizophrenic symptoms, including abnormalities social contacts, autism, oligophrenia, speech pathologies after stroke, conditions created by stress, brain blood flow insufficiency, concurrent with neurological and mental abnormalities, attention dysfunctions, decrease of focus and attention, attention instability during mental stress, lowered workability of children and adults, menopause syndrome, Vertebrobasilar insufficiency, cerebral atherosclerosis, post stroke conditions, headaches of vascular etiology, memory dysfunctions, and children's and seniors attentions and speech dysfunctions (the formulations assists in assimilation and memorization of new information). The formulations may be recommendable at delays of mental or speech development, poor learning performance, or to improve conditions of patients with vascular brain diseases (arteriosclerosis' and hypertonic disease), increase moving and mental activity of the patients after stroke and brain injuries, to address depressive conditions of various etiology, including ones with asthenia and hypochondriac symptoms, alcoholic encephalopathy and organic central nervous system damage of various etiology, epilepsy with pronounced abnormalities of intellect-memory functions, or an inability or difficulty in maintaining a vegan lifestyle and abstain from foods of animal origin.

Some compositions will be formulated as a capsule or powder, and will comprise one or more peptides, and a set of free-form (free) amino acids. The set of free amino acids can include amino acids selected from a group comprising or consisting of Glutamic Acid, Beta-alanine, Asparagine, Leucine, Lysine, Glycine, Gamma Aminobutyric Acid (GABA), Glutamine, Arginine, Taurine, Tryptophan, Ornithine, Theanine, and Glutamine. The one or more peptides can comprise peptides of any suitable length, including peptides having 2-100 amino acids residues joined via a peptide bond, 2-50 amino acids residues joined via a peptide bond, 2-30 amino acids residues joined via a peptide bond, or 10-40 amino acids residues joined via a peptide bond. Some contemplated peptides include collagen peptides, NAP (davunetide), opioid peptides, IPH, AVN (made of glutamic acid, lysine, aspartic acid—molecular formula $C_{15}H_{26}N_4O_8$), AEN (made of glutamic acid, alanine, aspartic acid—molecular formula $C_{12}H_{19}N_3O_8$), AGAA (made of aspartic acid, glutamic acid, arginine, alanine—molecular formula $C_{18}H_{37}N_2O_{12}$), SNL, AG, IPH/AEN, IPH/AGAA, IPH/AVNm SNL/AG, and other combinations and peptide variations. Peptides, vitamins, coenzymes and adaptogens all serve as catalysts or harmonizers for amino acids.

Other advantages and benefits of the disclosed compositions and methods will be apparent to one of ordinary skill with a review of the following detailed description.

DETAILED DESCRIPTION

The detailed description is intended as a description of various embodiments and is not intended to represent the only embodiments in which the disclosure may be practiced. The detailed description includes specific details for the purpose of providing a thorough understanding of the embodiments. However, it will be apparent that those skilled in the art will be able to understand the disclosure without these specific details The present invention is generally directed towards amino acid and peptide compositions found to be effective in supporting brain health, preventing, treating, or relieving a sign or symptom associated with one or more conditions, diseases or disorders. Peptides in the composition surprisingly stimulate improved uptake or absorption of amino acids in the composition, even when present in relatively small amounts. Thus, compositions with peptides act much faster in quantities where just normal amino acids would lack efficacy.

Contemplated compositions may optionally include a B vitamin (e.g., vitamin B6) as a coenzyme to enhance the action of the peptides or amino acids. In formulations including peptides and a set of amino acids, a B vitamin may not be necessary but can increase the effectiveness of the composition. Without wishing to be bound by any particular theory, it is contemplated that a B vitamin and peptide combination may have a synergistic effect in the absorption of the amino acids also included in some compositions.

Compositions of the inventive subject matter can include other beneficial ingredients, such as shilajit (mineral pitch), a sugar (e.g., glucose), a fatty acid, ashwaganda, ginseng, magnesium stearate, or rodiola, each of which can act as a coenzyme, sliding agent, or adaptogen, which can, for example, have a tonifying and adaptogenic effect, or serve as a delivery system.

Exemplary Compositions

Cerebroptim Namur: Cerebroptim Namur™ comprises glycine, GABA, beta alanine, leucine, lysine, taurine, and any additional beneficial ingredients which serves as a harmonizer, delivery system, energetic, coenzyme, sliding agent, or adaptogen, and may be useful in preventing, treating, or relieving a sign or symptom associated with ADHD, various memory dysfunctions, learning disabilities, delays of psycho-speech development, asthenia of any etiology, tiredness, decreased productivity in learning or work, conditions of decreased physical and mental power or energy, negative schizophrenic symptoms, including abnormalities social contacts, autism, oligophrenia, speech pathologies after stroke, and conditions created by stress. In some aspects, a daily dose of Cerebroptim Namur capsules (e.g., 2-6 capsules, 4 capsules) can comprise glycine (within 20% of 800 mg, within 10% of 800 mg), GABA (within 20% of 600 mg, within 10% of 600 mg), beta alanine (within 20% of 200 mg, within 10% of 200 mg), L-leucine (within 20% of 200 mg, within 10% of 200 mg), L-lysine (within 20% of 200 mg, within 10% of 200 mg), L-taurine (within 20% of 200 mg, within 10% of 200 mg). Optionally, the capsules may comprise Vitamin B6 (e.g., between 5-11 mg). Viewed from another perspective, the ratio of Glycine:GABA:beta alanine:L-Leucine:L-Lysine:L-Taurine in the compositions can be 3.2-4.8:2.4-3.6:1:8-1.2:8-1.2:8-1.2. Optionally, the capsules may comprise one or more peptides (e.g., a peptide comprised of glutamic acid, lysine, aspartic—molecular formula $C_{15}H_{26}N_4O_8$), and the ratio of Glycine:GABA:beta alanine:L-Leucine:L-Lysine:L-Taurine:peptides in the compositions can be 3.2-4.8:2.4-3.6:1:8-1.2:8-1.2:8-1.2:0.1-1—with the Glycine, GABA, beta alanine, L-Leucine, L-Lysine, and L-Taurine present as free amino acids.

Cerebroptim Niox: Cerebroptim Niox™ comprises arginine, glutamic acid, leucine, lysine, GABA, and any additional beneficial ingredient which serves as a harmonizer, delivery system, energetic, coenzyme, sliding agent, or adaptogen, and may be useful in preventing, treating, or relieving a sign or symptom associated with brain blood flow insufficiency, concurrent with neurological and mental abnormalities, attention deficit disorder (ADD), memory and attention dysfunctions, decrease of focus and attention, attention instability during mental stress, lowered workability of children and adults, menopause, vertebrobasilar insufficiency, cerebral atherosclerosis, post stroke conditions, and headaches of vascular etiology. In some aspects, a daily dose of Cerebroptim Niox capsules (e.g., 2-6 capsules, 4 capsules) can comprise L-Arginine (within 20% of 2,400 mg, within 10% of 2,400 mg), L-Glutamic Acid (within 20% of 300 mg, within 10% of 300 mg), L-Leucine (within 20% of 300 mg, within 10% of 300 mg), L-Lysine (within 20% of 300 mg, within 10% of 300 mg), and GABA (within 20% of 300 mg, within 10% of 300 mg). Optionally, the capsules may comprise Vitamin B6 (e.g., between 8-16 mg). Viewed from another perspective, the ratio of L-Arginine:L-Glutamic Acid:L-Leucine:L-Lysine:GABA in the compositions can 7-9:1:8-1.2:8-1.2:8-1.2. Optionally, the capsules may comprise one or more peptides (e.g., a peptide comprised of glutamic acid, lysine, aspartic—molecular formula $C_{15}H_{26}N_4O_8$), and the ratio of L-Arginine:L-Glutamic Acid: L-Leucine:L-Lysine:GABA:peptides in the compositions can be 7-9:1:8-1.2:8-1.2:8-1.2:0.1-1—with the L-Arginine, L-Glutamic Acid, L-Leucine, L-Lysine, and GABA present as free amino acids.

Cerebroptim Relasma: Cerebroptim Relasma™ comprises glycine, GABA, beta alanine, leucine, lysine, taurine, and any additional beneficial ingredient which serves as a harmonizer, delivery system, energetic, coenzyme, sliding agent, or adaptogen, and may be useful in preventing, treating, or relieving a sign or symptom associated with memory dysfunctions, and children's and seniors attentions and speech dysfunctions (the composition assisting in assimilation and memorization of new information). The composition may be recommended where there are delays of mental or speech development, or where poor learning performance is observed. The composition may improve conditions of patients with vascular brain diseases (arteriosclerosis' and hypertonic disease), and increase moving and mental activity of patients after a stroke or brain injuries. The composition may also be useful to alleviate depressive conditions of various etiology, including ones with asthenia and hypochondriac symptoms, alcoholic encephalopathy and organic central nervous system damage of various etiology, and epilepsy with pronounced abnormalities of intellect-memory functions. In some aspects, a daily dose of Cerebroptim Relasma capsules (e.g., 2-6 capsules, 4 capsules) can comprise glycine (within 20% of 1200 mg, within 10% of 1200 mg), GABA (within 20% of 900 mg, within 10% of 900 mg), beta alanine (within 20% of 300 mg, within 10% of 300 mg), L-leucine (within 20% of 300 mg, within 10% of 300 mg), L-lysine (within 20% of 300 mg, within 10% of 300 mg), L-taurine (within 20% of 300 mg, within 10% of 300 mg). Optionally, the capsules may comprise Vitamin B6 (e.g., between 5-20 mg). Viewed from another perspective, the ratio of Glycine:GABA:beta alanine:L-Leucine:L-Lysine:L-Taurine in the compositions can be 3.2-4.8:2.4-3.6:1:8-1.2:8-1.2:8-1.2. Optionally, the capsules may comprise one or more peptides (e.g., a peptide comprised of glutamic acid, lysine, aspartic—molecular formula $C_{15}H_{26}N_4O_8$), and the ratio of Glycine:GABA:beta alanine: L-Leucine:L-Lysine:L-Taurine:peptides in the compositions can be 3.2-4.8:2.4-3.6:1:8-1.2:8-1.2:8-1.2:0.1-1—with the Glycine, GABA, beta alanine, L-Leucine, L-Lysine, and L-Taurine present as free amino acids.

Some contemplated compositions will comprise the following: A set of amino acids comprising or consisting of L-Glutamic Acid, Beta Alanine, L-Asparagine, L-Leucine, L-Lysine, Glycine, Gama Aminobutyric Acid; Magnesium Stearate; and Vitamin B6.

Some contemplated compositions will comprise the following: A set of amino acids comprising or consisting of L-Arginine, L-Glutamic Acid, L-Leucine, L-Lysine, Gama Aminobutyric Acid; Magnesium Stearate; and Vitamin B6.

Some contemplated compositions will comprise the following: A set of amino acids comprising or consisting of Glycine, Gaba Aminobutyric Acid, Beta Alanine, L-Leucine, L-Lysine, L-Taurine; Magnesium Stearate; and Vitamin B6.

Some contemplated compositions will comprise the following: A set of amino acids comprising or consisting of Glycine, L-Tryptophan, Beta Alanine, L-Leucine, L-Lysine.

Some contemplated compositions will comprise the following: A set of amino acids comprising or consisting of Arginine, L-Ornithine, L-Theanine, Glutamic acid, L-Leucine, L-Lysine.

Some contemplated compositions will comprise the following: A set of amino acids comprising or consisting of Glutamine, Glycine, Beta alanine, L-Leucine, L-Lysine, L-Asparagin.

Some contemplated formulations/compositions will comprise the following: A set of amino acids comprising or consisting of L-Glutamic Acid, Beta Alanine, L-Asparagine, L-Leucine, L-Lysine, Glycine, Gama Aminobutyric Acid; Magnesium Stearate; Vitamin B6; and at least one peptide.

Some contemplated compositions will comprise the following: A set of amino acids comprising or consisting of L-Arginine, L-Glutamic Acid, L-Leucine, L-Lysine, Gama Aminobutyric Acid; Magnesium Stearate; Vitamin B6; and at least one peptide.

Some contemplated compositions will comprise the following: A set of amino acids comprising or consisting of Glycine, Gaba Aminobutyric Acid, Beta Alanine, L-Leucine, L-Lysine, L-Taurine; Magnesium Stearate; Vitamin B6; and at least one peptide.

Some contemplated compositions will comprise the following: A set of amino acids comprising or consisting of Glycine, L-Tryptophan, Beta Alanine, L-Leucine, L-Lysine; and at least one peptide.

Some contemplated compositions will comprise the following: A set of amino acids comprising or consisting of Arginine, L-Ornithine, L-Theanine, Glutamic acid, L-Leucine, L-Lysine; and at least one peptide.

Some contemplated compositions will comprise the following: A set of amino acids comprising or consisting of Glutamine, Glycine, Beta alanine, L-Leucine, L-Lysine, L-Asparagin; and at least one peptide.

The at least one peptide of the compositions described herein can comprise any number of different peptides (e.g., 1, 2, 3, 4, 5, at least 2, at least 3, at least 4, at least 5), including for example, collagen peptides, NAP (davunetide, an octapeptide), opioid peptides that bind to opioid receptors in the brain, IPH, AVN, AEN, AGAA, SNL, AG, IPH/AEN, IPH/AGAA, IPH/AVNm SNL/AG, and other combinations and peptide variations.

Some other contemplated formulations/compositions are provided in the Tables 1-12 below.

TABLE 1

| Content | Wt % |
| --- | --- |
| Glutamic acid | 0.1-90% |
| Beta alanine | 0.1-90% |
| Asparagine | 0.1-90% |
| Leucine | 0.1-90% |
| Lysine Hydrochloride | 0.1-90% |
| Glycine | 0.1-90% |
| Peptide | 0.1-90% |

TABLE 2

| Content | Wt % |
| --- | --- |
| Arginine | 0.1-90% |
| Glutamic acid | 0.1-90% |
| Leucine | 0.1-90% |
| Lysine Hydrochloride | 0.1-90% |
| Peptide | 0.1-90% |

TABLE 3

| Content | Wt % |
| --- | --- |
| Glycine | 0.1-90% |
| Beta alanine | 0.1-90% |
| Leucine | 0.1-90% |
| Lysine Hydrochloride | 0.1-90% |
| Peptide | 0.1-90% |

TABLE 4

| Content | Wt % |
| --- | --- |
| Glutamic acid | 32-35% |
| Beta alanine | 13-15% |
| Asparagine | 13-15% |
| Leucine | 11-13% |
| Lysine Hydrochloride | 11-13% |
| Glycine | 9-11% |
| Peptide | 5-11% |

TABLE 5

| Content | Wt % |
| --- | --- |
| Arginine | 65-72% |
| Glutamic acid | 8-9% |
| Leucine | 8-9% |
| Lysine Hydrochloride | 8-9% |
| Peptide | 5-11% |

TABLE 6

| Content | Wt % |
| --- | --- |
| Glycine | 50-55% |
| Beta alanine | 12-15% |
| Leucine | 12-15% |
| Lysine Hydrochloride | 12-15% |
| Peptide | 5-15% |

TABLE 7

| Content | Wt % |
| --- | --- |
| Glutamic acid | 33.2 |
| Beta alanine | 13.8 |
| Asparagine | 13.9 |
| Leucine | 11.8 |
| Lysine Hydrochloride | 11.8 |
| Glycine | 9.9 |
| Peptide | 5.7 |

TABLE 8

| Content | Wt % |
| --- | --- |
| Arginine | 68.7 |
| Glutamic acid | 8.7 |
| Leucine | 8.6 |
| Lysine Hydrochloride | 8.7 |
| Peptide | 5.6 |

TABLE 9

| Content | Wt % |
| --- | --- |
| Glycine | 52.6 |
| Beta alanine | 13.2 |
| Leucine | 13.2 |
| Lysine Hydrochloride | 13.3 |
| Peptide | 7.89 |

TABLE 10

| Content | Wt % |
| --- | --- |
| Glutamic acid | 32-35% |
| Beta alanine | 13-15% |
| Asparagine | 13-15% |
| Leucine | 11-13% |
| Lysine Hydrochloride | 11-13% |
| Glycine | 9-11% |
| Peptide complex IPH AVN | 5-10% |
| Loss on drying | ≤4% |
| Total plate count | ≤1000 cfu/g |
| Particle size range | ≥100% through 20 mesh |

TABLE 11

| Content | Wt % |
| --- | --- |
| Arginine | 65-72% |
| Glutamic acid | 8-9% |
| Leucine | 8-9% |
| Lysine Hydrochloride | 8-9% |
| Peptide complex IPH AVN | 5-11% |
| Loss on drying | ≤2% |
| Total plate count | ≤1000 cfu/g |
| Particle size range | ≥100% through 20 mesh |

TABLE 12

| Content | Wt % |
| --- | --- |
| Glycine | 50-55% |
| Beta alanine | 12-15% |
| Leucine | 12-15% |
| Lysine Hydrochloride | 12-15% |
| Peptide complex IPH AVN | 7-15% |
| Loss on drying | ≤2% |
| Total plate count | ≤1000 cfu/g |
| Particle size range | ≥100% through 20 mesh |

Many or all of the above exemplary compositions include L-leucine and L-lysine, which Applicant has discovered is an important combination that can cause brain function to improve.

Compositions of the inventive subject matter may be provided in any suitable dosage form, including for example, capsules, powders, ready-to-drink beverages, tablets, syrups, or injectable formulations.

Each capsule, tablet, or predetermined amount/serving of a powder, granule or liquid may have a therapeutically effective amount of the active ingredients of the composition. The compositions can also include inactive ingredients such as binding agents, binders or fillers; lubricants, sliding agent, or anti-adherent agent (such as magnesium stearate); disintegrants; or wetting agents.

Each amino acid of a composition may be present in any suitable amount, including for example, as 0.1-99 wt % of the amino acids in the composition, as 1-60 wt % of the amino acids in the composition, as 1-50 wt % of the amino acids in the composition, as 3-40 wt % of the amino acids in the composition, or as 8-35 wt % of the amino acids in the composition. As other examples, each amino acid of a composition may be present as 0.1-99 wt % of the Active Ingredients in the composition, as 1-60 wt % of the Active Ingredients in the composition, as 1-50 wt % of the Active Ingredients in the composition, as 3-40 wt % of the Active Ingredients in the composition, or as 8-35 wt % of the Active Ingredients in the composition. As used herein, the term "Active Ingredients" refers to amino acids and peptides in a composition, although it is contemplated that other active components may be included in contemplated compositions.

Each peptide of a composition, when present, may be present in any suitable amount, including for example, 0.1-20 wt % of the Active Ingredients in the composition, 0.1-15 wt % of the Active Ingredients in the composition, 0.1-10 wt % of the Active Ingredients in the composition, or 0.1-5 wt % of the Active Ingredients in the composition.

In some compositions, it is contemplated that the ratio of the wt % of the set of amino acids to the wt % of the peptide present will be between 99:1 and 3:1, between 20:1 and 5:1, between 12:1 and 5:1, or between 20:1 and 8:1.

Where magnesium stearate is included as an anti-adherent, it may be present in the composition in any suitable amount. For example, an oral composition can include about 0.1 to about 10% by weight magnesium stearate, about 0.5 to about 5% by weight magnesium stearate, or about 0.5-1% by weight magnesium stearate.

Where a B vitamin is included, it may be present in the composition in any suitable amount. For example, an oral composition can include about 0.1 to about 10% by weight vitamin B6, about 0.5 to about 5% by weight vitamin B6, or about 0.5-1% by weight vitamin B6.

A therapeutically effective amount of the composition may be administered to a subject that shows a sign or symptom associated with one or more conditions, including for example, attention deficit/hyperactivity disorder, memory dysfunctions, learning disabilities, delays in speech development, depression, or epilepsy, or any of the signs, symptoms or conditions discussed in this application. The compositions can be administered in a variety of dosing regimens to achieve the desired therapeutic effect. One of skill in the art will readily be able to determine a dosing protocol for optimal effects by monitoring the patient or user.

Additionally or alternatively, contemplated compositions can be consumed by individuals making a transition to a vegan or vegetarian lifestyle to ease or facilitate the transition. Without wishing to be bound by any particular theory, Applicant has found that the specific combination of amino acids and peptides in the amounts contemplated herein may signal a person's brain that further amino acids from animal sources are not needed.

The present invention also provides methods in which any of the formulations/compositions as described above and herein are used for the prevention or treatment of various conditions, or to improve cognitive function.

In one aspect of the inventive subject matter, a method of providing a product for human consumption will include a step of providing or including a quantity of a combination of free amino acids and at least one peptide in a product for human consumption, wherein the quantity is effective to improve cognitive function in a manner that can be tested via an intelligence test when the product is ingested at a recommended dosage and schedule. In a further step, a person can then be instructed to orally administer the product at the recommended dosage and schedule to improve cognitive function.

In another aspect, a method of providing a product for human consumption will include a step of providing or including a quantity of a combination of free amino acids and at least one peptide in a product for human consumption, wherein the quantity is effective to prevent, treat, or relieve a sign or symptom associated with one or more conditions, including for example, attention deficit/hyperactivity disorder, memory dysfunctions, learning disabilities, delays in speech development, depression, epilepsy, schizophrenia, autism, oligophrenia, speech pathologies after stroke, conditions created by stress, brain blood flow insufficiency, concurrent with neurological and mental abnormalities, attention dysfunctions, decrease of focus and attention, attention instability during mental stress, lowered workability of children and adults, menopause syndrome, Vertebrobasilar insufficiency, cerebral atherosclerosis, post stroke conditions, headaches of vascular etiology, memory dysfunctions, or children's and seniors attentions and speech dysfunctions.

While not limiting to the inventive subject matter, it is generally preferred that the quantity of amino acids comprises free amino acids and at least one peptide. Where the quantity of amino acids is provided in capsule form, it is further generally preferred that the dosage and schedule are selected such that the total daily number of capsules the user takes does not exceed 12 capsules, more preferably not to exceed 8 capsules, 6 capsules, 4 capsules, or even 2 capsules. Thus, in especially contemplated aspects, the product is formulated as a nutritional supplement, wherein the supplement is formulated to provide between 0.5 and 1 g of free amino acids and between 0.25 and 50 mg of peptides in a daily dose in which no more than 8 capsules are ingested by the user.

In another contemplated aspect of the inventive subject matter, a method of improving cognitive function or preventing, treating, or relieving a sign or symptom associated with one or more conditions such as those set forth above will include a step of administering to a person in need thereof a combination of free amino acids and peptides at a dosage and schedule effective to improve cognitive function or reduce at least one sign or symptom associated with at least one of attention deficit/hyperactivity disorder, memory dysfunctions, learning disabilities, delays in speech development, depression, epilepsy, schizophrenia, autism, oligophrenia, speech pathologies after stroke, conditions created by stress, brain blood flow insufficiency, concurrent with neurological and mental abnormalities, attention dysfunctions, decrease of focus and attention, attention instability during mental stress, lowered workability of children and adults, menopause syndrome, Vertebrobasilar insufficiency, cerebral atherosclerosis, post stroke conditions, headaches of vascular etiology, memory dysfunctions, and children's and seniors attentions and speech dysfunctions.

In a still further preferred aspect of the inventive subject matter, a method of providing a nootropic formulation as described herein will have a step of providing free amino acids and at least one peptide in the nootropic formulation in a quantity effective to increase or improve at least one of mental alertness, speech, and mood when the nootropic formulation is ingested at a recommended dosage and schedule. A further step can comprise a person being instructed to orally administer the stimulant at the recommended dosage and schedule to so increase or improve at least one of mental alertness, speech, and mood. It is generally preferred that the dosage and schedule are selected such that the total daily intake of the nootropic formulation provides between 0.5 and 1 g of free amino acids and between 0.25 and 50 mg of peptides in a daily dose.

The composition can be administered one, two, three times a day, or at any other suitable frequency. It is contemplated that the composition will be administered repeatedly or on an ongoing basis as needed or desired. Intermittent administration can also be used, wherein the composition is administered to the subject only sporadically with a specified time period between dosages. Thus, in some examples, there could be a one-day interval, a two or a three-day interval between any two days on which the composition is administered to the subject. Administration can be continued so long as a desired effect is achieved.

Experimental Data

Nootropic compositions can comprise an amino-acid and pyridoxine combination. The challenge with this combination is the amount of the material and time needed for the formulation to take effect in a subject. It can take 2-3 grams of each variation of the formulations to work. This translates into 4-6 capsules per variation. Taking into consideration that there are multiple variations of formulations, it creates a high burden on a consumer of the product as they have to take sometimes between 12 and 18 capsules (or even more) per day or per dose. On average, it was found that it can take 2-4 weeks of daily use of the amino-acid and pyridoxine combination formulations to produce notable results. This circumstance makes the burden on consumers immense, and due to frustration, most either give up entirely or diminish the dose, which makes it ineffective.

Applicant's objective was to reduce the amount of time, discipline and consumption required for the formulation to work, and to increase efficacy. Applicant surprisingly discovered that including one or more peptides with amino acids and pyridoxine in formulations can reduce the amount of time it takes for the formulation to take effect, and significantly enhance the functions of brain systems (e.g., glutamate system, Nitric oxide, GABA, Dopamine system) beyond what has been achieved by known nootropics. To gauge efficacy, Applicant used a standardized intelligence test, the Kaufman Brief Intelligence Test (KBIT-2).

KBIT-2 is a valid measure of verbal and non-verbal intelligence. The test is reliable, as it was developed based on a representative sample of 2120 examinees at 113 sites in 34 states and in the District of Columbia. The test is described as valid and reliable in peer-review publications, and is routinely administered by clinical psychologists, educational phycologists, guidance diagnosticians, and counselors.

Applicant's study verified that its peptide-based amino-acid nootropic formulations are superior to plain amino-acid-based nootropics. 15 individuals participated in the study, and were divided into three groups of 5 people. No participant had previously taken nootropics or any supplements used for the improvement of cognitive function. Further, no participant had previous experience with KBIT-2. Only the nonverbal component of the KBIT-2 test was conducted to avoid educational or cultural bias against any of the testing subjects. The experiment lasted 30 days, with testing every 15 days of all of the subjects.

The study included average fluid intelligence subjects, with very narrow tolerance from the absolute average score of 100 on the KBIT-2 scale. All testing subjects agreed not to prepare for the tests or retests, and not to consume any other nootropic supplements or stimulants like caffeine or nicotine. Subjects in the control group did not take any amino-acid formulations. Subjects in the experimental group 2 consumed 9 grams or six capsules of each of Namur, Niox, and Relasma formulations per day. Subjects in the experimental group 3 consumed 3 grams or two capsules of each of Namur, Niox, and Relasma formulations per day, but with the capsules comprising a peptide comprising about 5% of the daily dose, the peptide comprising glutamic acid, lysine, aspartic acid—molecular formula $C_{15}H_{26}N_4O_8$. Test results were not revealed to the subjects so as to not promote competitiveness or frustration with test results. The study involved the part of the test, which tests Fluid Intelligence. Fluid Intelligence is only minimally dependent on previous knowledge and is a representation of the mental processes such as memory, reasoning, classification, and analysis Results of the study are shown in Table 10 below:

TABLE 10

|  | Initial testing KBIT-2 score | Day 15 test KBIT-2 score | Day 30 test KBIT-2 score |
|---|---|---|---|
| Group 1 Control |  |  |  |
| Subject 1 | 98 | 94 | 98 |
| Subject 2 | 105 | 107 | 103 |
| Subject 3 | 100 | 100 | 103 |
| Subject 4 | 96 | 96 | 96 |
| Subject 5 | 98 | 100 | 98 |
| Average | 99.4 | 99.4 | 99.6 |
| Group 2 Experiment |  |  |  |
| Subject 1 | 103 | 107 | 109 |
| Subject 2 | 100 | 103 | 109 |
| Subject 3 | 98 | 100 | 105 |
| Subject 4 | 96 | 98 | 98 |
| Subject 5 | 100 | 100 | 105 |
| Average | 99.4 | 101.6 | 105.2 |
| Average difference vs. control group 1 | 0 - base phase | 2.2 | 5.6 |
| Average difference vs. control group 1 (%) | 0% base phase | 2.21% | 5.62% |
| Group 3 Experiment |  |  |  |
| Subject 1 | 98 | 111 | 119 |
| Subject 2 | 100 | 105 | 113 |
| Subject 3 | 98 | 107 | 116 |
| Subject 4 | 96 | 107 | 115 |
| Subject 5 | 105 | 113 | 121 |
| Average | 99.4 | 108.6 | 116.8 |
| Average difference vs. control group 1 | 0 phase base | 9.2 | 17.2 |
| Average difference vs. control group 1 (%) | 0% base phase | 9.25% | 17.26% |
| Average difference vs. experimental group 2 | 0 phase base | 7 | 11.6 |
| Average difference vs. experimental group 2 (%) | 0% base phase | 6.88% | 11.02% |

Discussion and study results. Unsurprisingly there was no significant change in the scores of subjects in Group 1 over the 30 days. A positive Fluid Intelligence dynamic in both experimental Groups 2 and 3 is evident. Comparing experimental Group 2 with experimental Group 3, we see that at a Day 15 test, all subjects in Group 3 had an increase in score that exceeded any of the increases in scores of the subjects of Group 2 between the initial test and the Day 15 test. Similarly, we see that at a Day 30 test, all subjects in Group 3 had an increase in score that exceeded any of the increases in scores of the subjects of Group 2 between the Day 15 and the Day 30 tests. The study results demonstrate time and material savings benefit of peptide-based formulations over the formulations without peptides. The study results proves the superiority of a peptide-based formulation in terms of efficacy, time-saving with fewer capsules used per individual per dose or per day.

Thus, specific examples of amino acid and peptide compositions have been disclosed. It should be apparent, however, to those skilled in the art that many more modifications besides those already described are possible without departing from the inventive concepts herein. While examples and variations of the many aspects of the invention have been disclosed and described herein, such disclosure is provided for purposes of explanation and illustration only. Thus, various changes and modifications may be made without departing from the scope of the claims. For example, not all of the components described in the formulations are necessary, and the invention may include any suitable combinations of the described components, and the general amounts or concentrations of the components of the invention may be modified. Accordingly, embodiments are intended to exemplify alternatives, modifications, and equivalents that may fall within the scope of the claims. The invention, therefore, should not be limited, except to the following claims, and their equivalents.

Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

The word "exemplary" is used herein to mean "serving as an example, instance, or illustration." Any aspect described herein as "exemplary" is not necessarily to be construed as preferred or advantageous over other aspects. Unless specifically stated otherwise, the term "some" refers to one or more.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise.

Combinations such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C.

Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, where any such combinations may contain one or more member or members of A, B, or C.

All structural and functional equivalents to the components of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. An oral composition, comprising:
 a set of free amino acids consisting of Glycine, GABA, Beta Alanine, Leucine, Lysine, and Taurine;
 at least one peptide;
 a Vitamin B6;
 wherein the wt % of the set of free amino acids to the wt % of the at least one peptide present in the composition is between 25:1 and 15:1; and
 wherein the Vitamin B6 comprises about 0.1 to about 10 wt % of the composition.

2. The composition of claim 1, wherein the at least one peptide includes no more than 25 amino acids.

3. The composition of claim 1, further comprising an anti-adherent.

4. The composition of claim 3, wherein the anti-adherent is magnesium stearate.

5. The composition of claim 1, wherein the at least one peptide comprises glutamic acid, lysine, and aspartic acid.

6. The composition of claim 1, wherein the composition comprises a therapeutically effective amount of the set of free amino acids and the at least one peptide to improve cognitive function in a manner that can be tested via an intelligence test when the composition is ingested at a recommended daily dosage for a period of 30 days.

7. An oral composition, comprising:
 a set of free amino acids consisting of Arginine, Glutamic acid, Leucine, Lysine, and GABA;
 at least one peptide;
 a Vitamin B6;
 wherein the wt % of the set of free amino acids to the wt % of the at least one peptide present in the composition is between 25:1 and 15:1; and
 wherein the Vitamin B6 comprises about 0.1 to about 10 wt % of the composition.

8. An oral composition, comprising:
 a set of free amino acids consisting of L-Glutamic Acid, Beta Alanine, L-Asparagine, L-Leucine, L-Lysine, Glycine, and GABA;
 at least one peptide;
 a Vitamin B6;
 wherein the wt % of the set of free amino acids to the wt % of the at least one peptide present in the composition is between 25:1 and 15:1; and
 wherein the Vitamin B6 comprises about 0.1 to about 10 wt % of the composition.

9. An oral composition, comprising:
 a set of free amino acids consisting of L-Arginine, L-Glutamic acid, L-Leucine, L-Lysine and GABA;
 at least one peptide;
 a Vitamin B6;
 wherein the wt % of the set of free amino acids to the wt % of the at least one peptide present in the composition is between 25:1 and 15:1;
 wherein the Vitamin B6 comprises about 0.1 to about 10 wt % of the composition;
 wherein the composition comprises a therapeutically effective amount of the set of free amino acids and the at least one peptide to improve cognitive function in a manner that can be tested via an intelligence test when the composition is ingested at a recommended daily dosage for a period of 30 days; and
 wherein the recommended daily dosage comprises within 20% of 2,400 mg of L-Arginine, within 20% of 300 mg of L-Glutamic Acid, within 20% of 300 mg of L-Leucine, within 20% of 300 mg of L-Lysine, and within 20% of 300 mg of GABA.

* * * * *